(12) United States Patent
Tiedtke

(10) Patent No.: US 9,037,252 B2
(45) Date of Patent: May 19, 2015

(54) VISUAL PROSTHESIS AND RETINA STIMULATION DEVICE FOR SAME

(75) Inventor: Hans-Jürgen Tiedtke, Bonn (DE)

(73) Assignee: PIXIUM VISION SA, Paris (FR)

(*) Notice: Subject to any disclaimer, the term of this patent is extended or adjusted under 35 U.S.C. 154(b) by 39 days.

(21) Appl. No.: 13/203,710

(22) PCT Filed: Feb. 27, 2009

(86) PCT No.: PCT/EP2009/001409
§ 371 (c)(1),
(2), (4) Date: Dec. 9, 2011

(87) PCT Pub. No.: WO2010/097096
PCT Pub. Date: Sep. 2, 2010

(65) Prior Publication Data
US 2012/0101550 A1    Apr. 26, 2012

(51) Int. Cl.
*A61N 1/08* (2006.01)
*A61N 1/36* (2006.01)
*A61N 1/05* (2006.01)

(52) U.S. Cl.
CPC ........... *A61N 1/36046* (2013.01); *A61N 1/0543* (2013.01)

(58) Field of Classification Search
None
See application file for complete search history.

(56) References Cited

U.S. PATENT DOCUMENTS 7,149,586 B2    12/2006  Greenberg
8,503,713 B2 *   8/2013  Ziemeck et al. .............. 382/100

(Continued)

FOREIGN PATENT DOCUMENTS

DE    102006060045    6/2008
GB       1 553 969    10/1979

(Continued)

OTHER PUBLICATIONS

International Preliminary Report on Patentability issued in PCT/EP2009/001409 on Sep. 9, 2011.

*Primary Examiner* — Brian T Gedeon
*Assistant Examiner* — Ankit Tejani
(74) *Attorney, Agent, or Firm* — Sam K. Tahmassebi; TechLaw LLP

(57) ABSTRACT

The present invention provides a visual prosthesis comprising: image capture means for capturing an image from a surrounding environment; image processing means for processing the image and converting the image into a transmissible image signal; signal processing means for processing and converting the image signal into a stimulation signal; and a retina stimulation device (10) adapted to stimulate the retina of both left and right eyes in accordance with the stimulation signal. The retina stimulation device (10) comprises a left-side stimulation unit (11) having an electrode array (12) for stimulating the retina of the left eye, and a right-side stimulation unit (11') having an electrode array (12') for stimulating the retina of the right eye, with the left-side stimulation unit (11) having a configuration which is reversed with respect to a configuration of the right-side stimulation unit (11'). Furthermore, the electrode array (12) has a plurality of individual electrodes (15) distributed in a predetermined pattern across a substrate (16) of the electrode array for stimulating the nerve cells of the retina. The electrode array substrate (16) is elongate in a lateral or transverse direction, namely in a medial-lateral direction with respect to an implantation orientation, such that the electrode array has a height-to-width ratio of less than 1, preferably less than 0.8, more preferably in the range of 0.6 to 0.2, and most preferably in the range of about 0.5 to about 0.3.

19 Claims, 1 Drawing Sheet

(56) References Cited

U.S. PATENT DOCUMENTS

| | | |
|---|---|---|
| 2003/0097165 A1 | 5/2003 | Krulevitch et al. |
| 2003/0158588 A1 | 8/2003 | Rizzo et al. |
| 2003/0233134 A1 | 12/2003 | Greenberg |
| 2006/0247754 A1 | 11/2006 | Greenberg |
| 2008/0281377 A1 | 11/2008 | Caspi et al. |

FOREIGN PATENT DOCUMENTS

| | | |
|---|---|---|
| GB | 1553969 | 10/1979 |
| WO | 00/56393 A1 | 9/2000 |
| WO | 0056393 | 9/2000 |
| WO | WO 2008074478 A2 * | 6/2008 |

* cited by examiner

VISUAL PROSTHESIS AND RETINA STIMULATION DEVICE FOR SAME

RELATED APPLICATIONS

This application is filed under 35 U.S.C. §371 as the U.S. national phase of International Application PCT/EP2009/001409, filed Feb. 27, 2009, which designated the U.S. The entire disclosure of both applications, including the drawings, is hereby incorporated herein by reference.

TECHNICAL FIELD

The present invention relates to a visual prosthesis, and more particularly to a visual prosthesis for restoring vision to patients afflicted with certain diseases leading to degeneration of the retina. The invention also relates to a retina stimulation device for use in such a visual prosthesis.

BACKGROUND ART

In the course of about the last fifteen years, concerted efforts have been made to develop techniques and devices for restoring vision in patients afflicted by certain diseases. In patients suffering from macula degeneration and retinitis pigmentosa, both of which diseases lead to a loss of retina function over a period of time and ultimately cause total blindness, it has been discovered that substantial parts of the nervous system of the eye, including the optic nerve and the sub-retinal neurons, actually remain intact and fully functional. Since the early days of research and development in this field, therefore, a number of different techniques and solutions have been proposed for taking advantage of this retained retinal functionality.

One such solution proposes an implant containing photodiodes designed to convert the light incident on the retina into electrical stimuli for the retinal ganglion cells. In practice, however, the energy level of the incident light proved to be insufficient to provoke a depolarization of the nerve cells. An alternative approach has been to capture an image using, for example, a camera and to process the image to match a grid of electrodes positioned on or below the surface of the retina and then to stimulate the nerve tissues via corresponding signals to the electrodes. This latter approach has provided promising results and forms the basis for much on-going research and development in this field.

In German Patent Publication No. DE 10 2006 060045 A1, for example, a system has been proposed in which additional data relating to the relative position in space of the object are processed during the capture and generation of the image signal.

It remains a goal of researchers, however, to develop a visual prosthesis or system that provides patients with an experience of vision that more closely approximates natural sight.

SUMMARY OF THE INVENTION

In pursuance of the above goal, the present invention provides a visual prosthesis and a retina stimulation device as defined in the independent claims. Preferred features of the invention are recited in the dependent claims.

According to one aspect of the present invention, a visual prosthesis for a patient is provided, which comprises:
  image capture means for capturing an image from a surrounding environment;
  image processing means for processing the image and converting the image into a transmissible image signal;
  signal processing means for processing and converting the image signal into at least one stimulation signal; and
  a retina stimulation device adapted to stimulate the retina of both left and right eyes of the patient in accordance with the at least one stimulation signal.

In a preferred form of the invention, the retina stimulation device comprises a left-side stimulation unit having an electrode array for stimulating the retina of the left eye, and a right-side stimulation unit having an electrode array for stimulating the retina of the right eye. Preferably, the left-side stimulation unit has a configuration which is reversed with respect to a configuration of the right-side stimulation unit. In this regard, the inventor has determined that such a reversed configuration of the left-side and right-side stimulation units is particularly advantageous for the implantation of the stimulation units in the respective eyes of the patient and, thus, for the realization of stereoscopic retina stimulation.

In a preferred form of the invention, each of the left- and right-side stimulation units further comprises an elongate connection for conducting or conveying the at least one stimulation signal to the electrodes of the respective electrode array. That is, each of the electrode arrays is adapted to communicate with the signal processing means, preferably via its own respective elongate connection. The connection may therefore comprise a cable, such as a ribbon cable, which provides electrical communication between the electrodes of a respective electrode array and the signal processing means. The elongate connection extends to and/or from the respective electrode array at an angle of between 0° and 90°, preferably between 20° and 70°, and more preferably between 30° and 60°, relative to a lateral or transverse direction of the electrode array, e.g. a medial-lateral direction with respect to an implantation orientation of the electrode array. Most preferably, the elongate connection extends to and/or from the respective electrode array at an angle of between about 40° and 50° relative to a lateral or transverse direction of the electrode array.

This particular arrangement of the elongate connection (e.g. cable) relative to each of the electrode arrays results in the components of the visual prosthesis according to the invention being specifically adapted to be implanted in a desired orientation between the external eye-muscles *M rectus superior* and *M rectus lateralis*. By also tailoring the configuration of the left-side stimulation unit and the right-side stimulation unit to have a reversed configuration with respect to one another, the same implantation orientation can be achieved for both of the left and right eyes. In a particularly preferred form of the invention, the configuration of the left-side stimulation unit is a mirror image of the configuration of the right-side stimulation unit.

In a preferred form of the invention, the signal processing means of the visual prosthesis comprises a left-side signal processing means for processing and converting the at least one image signal into a stimulation signal for the left-side stimulation unit (i.e. for the left-side electrode array), and a right-side signal processing means for processing and converting the at least one image signal into a stimulation signal for the right-side stimulation unit (i.e. for the right-side electrode array).

Similarly, the image capture means of the visual prosthesis may comprise a left-side image capture means and a right-side image capture means. Each image capture means is preferably in the form of a camera or video imaging device. For example, the image capture means may include a CCD or a CMOS device. Thus, the image processing means of the visual prosthesis may also comprise a left-side image processing means and a right-side image processing means, the left-side image processing means being for processing and converting the image from the left-side image capture means into an image signal for transmission to the left-side signal processing means, and the right-side image processing means being for processing and converting the image from the right-side image capture means into an image signal for transmission to the right-side signal processing means.

By generating left and right stimulus signals and stimulating the retinas of both the left and right eyes, the present invention is able to produce a stereoscopic visual experience for the patient that more closely approximates natural sight.

In a preferred form of the invention, the electrode array of each stimulation unit has an elongated configuration in the lateral or transverse direction. That is, when adapted for orientation in the medial-lateral direction or plane of the human body, each of the left-side and right-side electrode arrays has a height-to-width ratio of less than 1, and preferably less than 0.8, and more preferably less than 0.6, but preferably not less than about 0.2.

In a preferred form of the invention, each electrode array comprises a plurality of individual electrodes distributed in a predetermined pattern across a substrate for stimulating the nerve cells of the retina, wherein the substrate of the electrode array defines the elongate shape of the retina stimulation device in the medial-lateral direction. The shape of the electrode array substrate may include straight sides and/or curved sides. For example, the electrode array may be rectangular with straight sides, rectangular with curved (e.g. concave and/or convex) sides, or elliptical.

With regard to the elongated configuration of each electrode array in the lateral or transverse direction, the inventor has recognized that the conventional square electrode arrays do not achieve an optimum stimulation of the available nerve tissue in the retina. By re-designing the electrode array(s) of the retina stimulation device to have a significantly greater extent in the medial-lateral direction (i.e. width or breadth) than in the vertical direction (i.e. height), the inventor has been able to activate a greater number of retinal ganglion cells and achieve a greater virtual field of vision for a given area of the electrode array. As such, the invention provides a more optimal stimulation of the retina nerve cells and a more efficient electrode array configuration.

More particularly, the inventor has ascertained that an optimized use of the retina surface (e.g. the epi-retinal surface) can be achieved by restricting the electrodes of the electrode array to an elongate substrate or strip having a height-to-width ratio in the range of about 0.6 to about 0.2, and more preferably in the range of about 0.5 to about 0.3, in the transverse or medial-lateral direction. In this connection, it will be noted that an epi-retinal implant is applied to the surface of the retina. The retina does not have a planar surface, but rather a curved, approximately ellipsoidal surface at the rear inner wall of the posterior chamber of the eye. The elongate form of the electrode array substrate developed in this case not only provides an optimized stimulation of the retinal cells for a given area of the electrode array substrate, it has also been found to provide a better, more consistent, and more enduring conformity of the electrode array with the retinal tissue.

According to another aspect of the invention, a retina stimulation device for use in a retinal implant, and preferably for use in a visual prosthesis according to the invention, is provided. The retina stimulation device includes at least one stimulation unit for implantation into an eye of a patient, and comprises an electrode array having a plurality of individual electrodes for stimulating the nerve cells of the retina, the electrodes being distributed in a predetermined pattern across an electrode array substrate. The electrode array substrate is elongate in a lateral or transverse direction of the array, namely in a medial-lateral direction with respect to an implantation orientation, such that the electrode array has a height-to-width ratio of less than 1. As noted above, when adapted for orientation in the medial-lateral direction or plane of the human body, the electrode array preferably has a height-to-width ratio of less than 0.8, and more preferably less than 0.6. The height-to-width ratio of the electrode array may even be 0.4 or less, but is desirably not less than 0.2.

In a preferred form of the invention, the at least one stimulation unit of the retina stimulation device further comprises an elongate connection which extends to and/or from the substrate of the electrode array for communication with a signal processing means to provide a stimulation signal to the electrodes. Thus, the elongate connection may, for example, comprise a cable, such as a ribbon cable, to provide electrical communication between the electrodes of the electrode array and the signal processing means of a visual prosthesis. The elongate connection extends from the electrode array at an angle of between 0° and 90°, preferably between 20° and 70°, and more preferably between 30° and 60°, relative to the lateral or transverse direction of the electrode array, and in particular relative to the medial-lateral direction with respect to the implantation orientation. Most preferably, the elongate connection extends from the electrode array at an angle of between about 40° and 50° relative to the lateral or transverse direction.

In a preferred form of the invention, the retina stimulation device comprises a left-side stimulation unit having an electrode array for stimulating the retina of the left eye and a right-side stimulation unit having an electrode array for stimulating the retina of the right eye, wherein the left-side stimulation unit has a configuration which is reversed compared with a configuration of the right-side stimulation unit. More preferably, the configuration of the left-side stimulation unit is a mirror image of the configuration of the right-side stimulation unit. It will be appreciated, however, that the retina stimulation device of the invention may comprise a single stimulation unit for stimulating the retina in one eye of a patient.

BRIEF DESCRIPTION OF THE DRAWINGS

The above and further features and advantages of the present invention will become more apparent from the following detailed description of particular embodiments of the invention with reference to the accompanying drawing figures, in which like components are designated with like reference characters, and in which.

DETAILED DESCRIPTION OF THE PREFERRED EMBODIMENTS OF THE INVENTION

Figure 1:
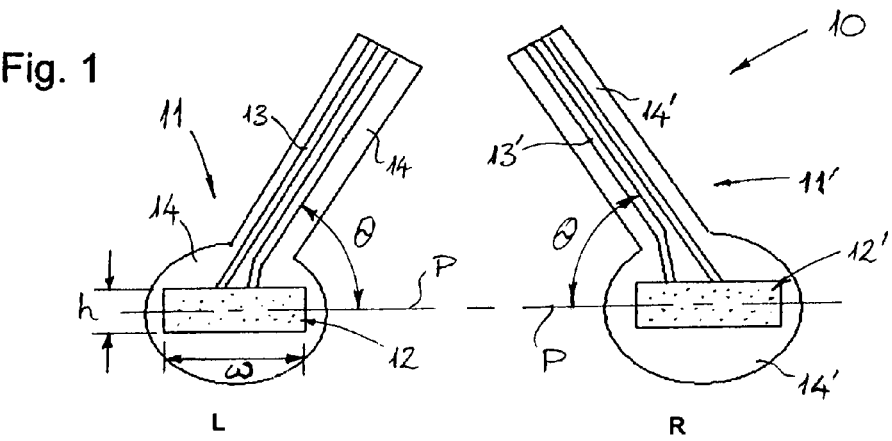
FIG. 1 is a schematic front view of a retina stimulation device according to an embodiment of the present invention, including left-side and right-side stimulation units, denoted by "L" and "R", respectively.

The visual prosthesis according to a preferred embodiment of the present invention incorporates both internal (i.e.

implanted) components and external (i.e. non-implanted) components. In particular, the system architecture of the visual prosthesis according to the invention generally reflects the state-of-the-art design, in which a device resembling a pair of glasses or spectacles incorporates image capture means for capturing an image of the environment surrounding the user. According to this particular embodiment of the invention, the spectacles (not shown) incorporate an image capture means in the form of a left-side camera and a right-side camera, the two cameras being spaced apart from one another at opposite (i.e. left and right) sides of the spectacles; for example, in or adjacent the respective arm members of the frame of the spectacles.

The visual prosthesis furthermore includes an external processor device (not shown) which is preferably designed to be carried by the user, for example, in a breast pocket or in a belt-mounted pouch. The processor device is operatively connected with the two cameras in the spectacles' frame and incorporates means for processing and converting each of the images generated by the left-side and right-side cameras into a left-side image signal and a right-side image signal, respectively.

The left- and right-side image signals are then transmitted to respective internal or implanted components of the visual prosthesis. In particular, the frame of the spectacles preferably incorporates left and right transmitter devices for wirelessly transmitting the image signals. In this connection, the visual prosthesis further includes a signal processing unit 20 implanted extraocularly for processing and converting the image signal transmitted from the image capture means into a stimulation signal. As can be clearly seen in FIG. 2 of the drawings, the visual prosthesis of the invention includes a left-side processing unit 20 and a right-side processing unit 20', each of which is mounted or implanted on an outer surface of the eyeball 1, attached to the sclera 2 between the *rectus superior* muscle 3 and the *rectus lateralis* muscle 4 of the eye.

Figure 2:
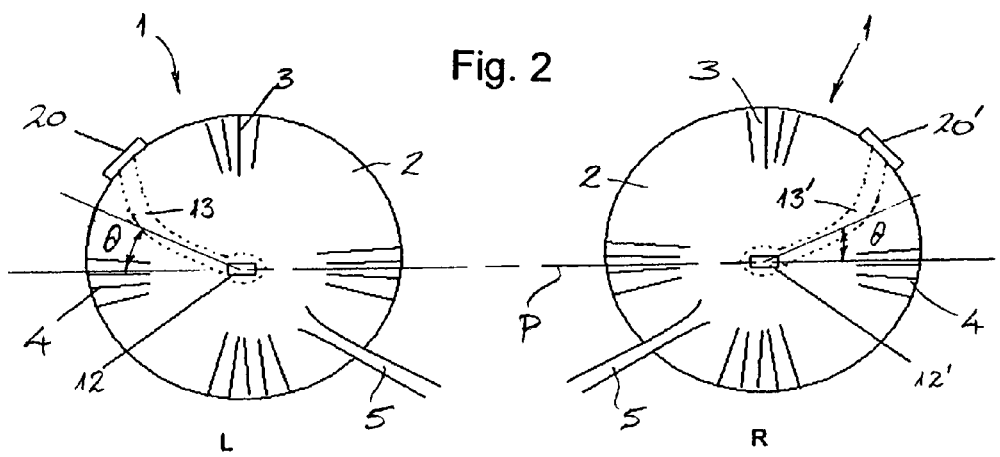
FIG. 2 is a schematic rear view of left and right eyes denoted by "L" and "R", respectively, with the retina stimulation device of FIG. 1 shown in an implanted state.

With reference now to both FIG. 1 and FIG. 2 of the drawings, a retina stimulation device 10 which is adapted to stimulate the nerve cells of the retina in a visual prosthesis according to the invention is illustrated. The retina stimulation device 10 includes a left-side stimulation unit 11 having a left-side electrode array 12 in electrical communication with the left-side processing unit 20 via an elongate connection 13 in the form of a ribbon cable. In a corresponding manner, the retina stimulation device 10 further includes a right-side stimulation unit 11' comprising a right-side electrode array 12' which is in electrical communication with the right-side processing unit 20' via another elongate connection 13', again in the form of a ribbon cable.

Each of the left- and right-side electrode arrays 12, 12' and its respective ribbon cable 13, 13' is coated with and/or encased in a film, sheath or membrane 14, 14' of a biocompatible polymer material, such as silicone, to protect the electrical circuits from the aqueous environment within the body. In this respect, it will be noted that the left- and right-side electrode arrays 12, 12' are substantially flat structures, having a very small thickness into the plane of drawing FIG. 1. That is, the left- and right-side stimulation units 11, 11' comprising the electrode arrays 12, 12' and their connecting ribbon cables 13, 13' together with the protective layer 14, 14' of polymer material have a dimension perpendicular to the plane of drawing FIG. 1 which is small compared to the dimensions in that plane.

As is clearly illustrated in FIG. 2 of the drawings, the electrode array 12, 12' for each of the left- and right-side stimulation units 11, 11' is adapted to be located in the macula region of the retina, e.g. in the region known as the fovea, approximately centrally of an inner surface at the rear of the posterior chamber of the eyeball. The electrode array 12, 12' is desirably applied epi-retinally, i.e. to the surface of the retina, as opposed to being implanted into the tissue of the retina or in a sub-retinal space. It should be noted, however, that a sub-retinal placement of the electrode array 12, 12' is also contemplated by the present invention. The optic nerve 5 for each of the left and right eyeballs 1 is represented schematically extending medially from a rear side of each eyeball.

In this connection, it will be noted that each of the left- and right-side electrode arrays 12, 12' has a generally rectangular configuration which is oriented such that each electrode array 12, 12' is elongate in a lateral or transverse direction, namely in a medial-lateral direction with respect to the eyeball 1, as denoted by the axis P. In particular, a width w of the electrode array 12 in the lateral or transverse direction (i.e. in the medial-lateral direction or plane P) is substantially larger than a height h of the electrode array 12, such that the height-to-width ratio of the electrode array 12 is in the range of about 0.5 to about 0.3. The inventor has ascertained that these proportions produce the most effective retina stimulation device in view, on the one hand, of maintaining the very thin, flexible electrode arrays 12, 12' in satisfactory contact with the curved, generally ellipsoidal tissue surface of the retina, and on the other hand, of activating the nerve cells of the retina sufficiently not only in the medial-lateral direction P, but also in the vertical direction to achieve a desired image reproduction.

As can be seen in FIG. 1 of the drawings, the elongate connections (i.e. ribbon cables) 13, 13' extend to and/or from each of the electrode arrays 12, 12' at an angle θ of between 30° and 60°, and more particularly between 40° and 50°. This particular angular orientation renders the retina stimulation device 10 of the invention specifically adapted for implantation in a region of the eye extending approximately centrally between the *rectus superior* muscle 3 and the *rectus lateralis* muscle 4. More specifically, the inventor has determined that the respective signal processing units 20, 20' can be advantageously implanted extraocularly attached to the outside of the sclera 2 approximately mid-way between the *rectus superior* muscle 3 and the *rectus lateralis* muscle 4. The angled orientation of the ribbon cables 13, 13' (i.e. the angle θ) relative to their respective electrode arrays 12, 12' thus significantly simplifies and improves the desired respective positioning of the components during implantation. (Note: The cables 13, 13' appear to follow a curved path in drawing FIG. 2 due to the fact that they follow the curvature of each eyeball 1.) In this respect, the skilled person will appreciate that the cables 13, 13' need not be perfectly straight, but may also be somewhat curved to enhance their conformity with the curvature of the eye.

Thus, the inventor has developed separate left- and right-side stimulation units 11, 11' that have a reverse configuration with respect to one another. In particular, as can be clearly seen in FIG. 1 of the drawings, the left-side stimulation unit 11 (denoted by "L") desirably has a configuration which is a mirror-image of the configuration of the right-side stimulation unit 11' (denoted by "R"). In this way, the left-side components of the visual prosthesis can be readily implanted at a corresponding position located symmetrically with respect to the right-side components of the prosthesis.

Figure 3:
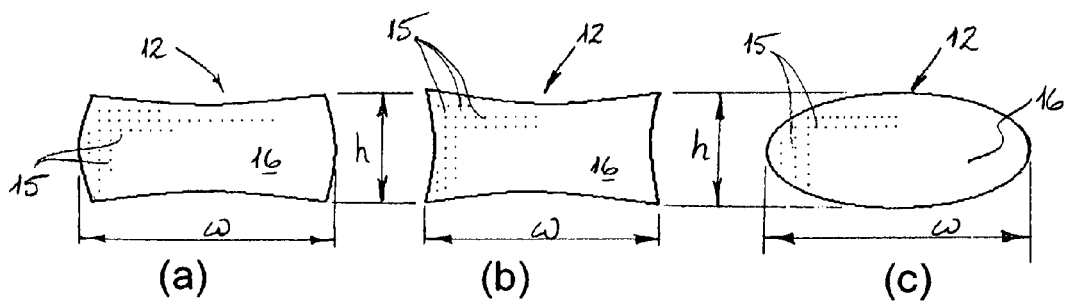
FIG. 3 shows schematic views of three different shapes (a) to (c) for an electrode array according to embodiments of the invention.

With reference now to FIG. 3 (*a*) to (*c*), different examples of an electrode array 12 of a retina stimulation device 10 according to the invention are illustrated. In each case, the electrode array 12 includes a plurality of individual electrodes 15 (here shown as points or dots indicating the tips or crosssections of the electrodes) for stimulating the nerve cells of the retina, with the individual electrodes being distributed in a predetermined pattern across a substrate 16 of the electrode array. With respect to the predetermined pattern, it will be noted that the individual electrodes 15 are more closely spaced in the region of the substrate 16 to be positioned at the fovea, with the separation or distance between the individual electrodes 15 increasing with distance from the fovea. Thus, if the centre area of the electrode array 12 is to be positioned at the fovea, then the individual electrodes 15 in the centre of the substrate 16 will be more closely spaced, with the electrodes becoming progressively further spaced apart towards the periphery of the substrate. Preferably, the increase in spacing between the individual electrodes 15 of the electrode array 12 (i.e. in the plane of the drawing) varies linearly (i.e. in a linear relationship) with the distance from the centre of the substrate 16. The electrodes 15 are desirably arranged in rows on the substrate 16 (e.g. straight rows extending in the medial-lateral direction P).

As noted above, the substrate 16 of the electrode array 12 is elongate in a transverse or lateral direction corresponding to the medial-lateral direction P in an implanted orientation. That is, a substantially more efficient and thereby more effective stimulation of the retina can be achieved with an electrode array having a height-to-width ratio (h/w) in the range of about 0.5 to about 0.2. This can be achieved with different shapes, including a straight-sided rectangular shape (as shown in FIGS. 1 and 2), a rectangular shape having concave sides and convex ends as shown in FIG. 3 (*a*), a rectangular shape having concave sides and concave ends as shown in FIG. 3 (*b*), as well as with an elliptical configuration as shown in FIG. 3 (*c*).

The individual electrodes 15 may be fabricated from copper, silver or gold, but gold is particularly preferred in view of its resistance to corrosion in an aqueous environment. The substrate 16 of the electrode array 12 is typically formed a polymer material, in particular a bio-compatible polymer material, such as silicone or parlyene.

It will be appreciated that the above discussion of particular embodiments of the invention with reference to the drawings is for illustrative purposes only. Accordingly, it will be appreciated that various modifications can be made in the embodiments described without departing from the scope of the invention as defined in the following claims.

The invention claimed is:

1. A visual prosthesis comprising:
   image capture means for capturing an image from a surrounding environment, wherein the image capture means is configured in the form of a left-side camera and a right-side camera, the two cameras being spaced part from one another at opposite sides of a pair of spectacles;
   image processing means for processing the image and converting the image into a transmissible image signal;
   signal processing means for processing and converting the image signal into at least one stimulation signal; and
   a retina stimulation device adapted to stimulate a retina of both left and right eyes in accordance with the at least one stimulation signal;
   wherein each of a left-side electrode array and a right-side electrode array has an elongated configuration in a lateral or transverse direction such that each of the left-side electrode array and the right-side electrode array has a height-to-width (h/w) of less than 0.8, and
   wherein the retina stimulation device comprises left-side stimulation unit and the right-side stimulation unit which comprise an elongate connection for conducting or conveying the at least one stimulation signal to electrodes of the respective electrode arrays, and wherein the elongate connection respectively extends to and/or from the respective electrode array at a predefined angle (θ) of between 0° and 90°, or between 20° and 70°, relative to a lateral or transverse direction (P) with respect to an implantation orientation of the electrode array, the elongate connections being configured for being arranged in a predefined angled configuration, and mirror-imaged.

2. The visual prosthesis of claim 1, wherein the left-side stimulation unit having a left-side electrode array for stimulating the retina of the left eye, and the right-side stimulation unit having a right-side electrode array for stimulating the retina of the right eye are arranged in a reversed configuration with respect to each other.

3. The visual prosthesis of claim 2, wherein the configuration of the left-side stimulation unit is a mirror-image of the configuration of the rightside stimulation unit.

4. The visual prosthesis of claim 2, wherein each of the left-side electrode array and the right-side electrode array has an elongated configuration in the lateral or transverse direction, namely in the medial-lateral direction (P), such that each said electrode array has a height-to-width (h/w) in the range of 0.6 to 0.2.

5. The visual prosthesis of claim 4, wherein a shape of the electrode substrate of the left-side electrode and the right-side electrode array includes straight sides and/or curved sides.

6. The visual prosthesis of claim 4, wherein the height-to-width ratio (h/w) is in the range of 0.5 to 0.3.

7. The visual prosthesis of claim 2, wherein each of the left-side electrode array and the right-side electrode array comprises a plurality of individual electrodes distributed in a predetermined pattern across a substrate of the corresponding electrode array for stimulating nerve cells of a retina, and wherein the substrate of the corresponding electrode defines an elongate shape of the retina stimulation device in the medial-lateral direction (P).

8. The visual prosthesis of claim 2, wherein the elongate connection provides electrical communication between electrodes of the left-side electrode array and the right-side electrode array and the signal processing means for conveying the at least one stimulation signal to the electrodes, wherein the elongate connection comprises a cable.

9. The visual prosthesis of claim 2, wherein the elongate connection extends from the left-side electrode array and the right-side electrode array at an angle (A) of between 20° and 70°, between 30° and 60°, or between 40° and 50° relative to the lateral or transverse direction.

10. The visual prosthesis of claim 9, wherein the elongate connection comprises a cable, which provides electrical communication between i) the electrodes of the left-side electrode array and the right-side electrode array and ii) the signal processing means.

11. The visual prosthesis of claim 2, wherein the lateral or transverse direction (P) is a medial-lateral direction, with respect to an implantation orientation of the left-side electrode array and the right-side electrode array.

12. The visual prosthesis of claim 2, wherein each of the left- and right-side electrode arrays and its respective elongate connection is coated with and/or encased in a film, sheath or membrane of a bio-compatible polymer material.

13. The visual prosthesis of claim 1, wherein each of the left-side electrode array and the right-side electrode array has an elongated configuration in the medial-lateral direction (P).

14. The visual prosthesis of claim 13, wherein the height-to-width ration of the left-side electrode array and the right-side electrode array is less than 0.6.

15. The visual prosthesis of claim 1, wherein the retina stimulation device has at least one stimulation unit comprising:
- an electrode array having a plurality of individual electrodes distributed in a predetermined pattern across a substrate of the electrode array for stimulating nerve cells of a retina,
- wherein a electrode array substrate of the left-side electrode array and the right-side electrode array is elongate in a lateral or transverse direction, namely in a medial-lateral direction (P) with respect to an implantation orientation, such that the electrode array has a height-to-width ratio (h/w) of less than 0.8.

16. The visual prosthesis of claim 15, wherein the left-side stimulation unit having an electrode array for stimulating the retina of the left eye and the right-side stimulation unit having an electrode array for stimulating the retina of the right eye are arranged in a reversed configuration with respect to each other.

17. The visual prosthesis of claim 16, wherein the configuration of the left-side stimulation unit is a minor image of the configuration of the right-side stimulation unit.

18. The visual prosthesis of claim 15, wherein the predetermined pattern comprises the electrodes being more closely spaced in a central region of the substrate of the left-side electrode and the right-side electrode array than at a periphery of the substrate of the left-side electrode array and the right-side electrode array.

19. The visual prosthesis of claim 15, wherein the electrodes are arranged in substantially straight rows and/or columns over the area of the electrode array substrate of the left-side electrode array and the right-side electrode array.

* * * * *